United States Patent
Gefen et al.

(10) Patent No.: US 9,720,477 B2
(45) Date of Patent: Aug. 1, 2017

(54) WEAK POWER SUPPLY OPERATION AND CONTROL

(71) Applicant: NANO-RETINA, INC., Wilmington, DE (US)

(72) Inventors: Ra'anan Gefen, Re'ut (IL); Tuvia Liran, Qiryat Tivon (IL)

(73) Assignee: NANO-RETINA, INC., Wilmington, DE (US)

(*) Notice: Subject to any disclaimer, the term of this patent is extended or adjusted under 35 U.S.C. 154(b) by 647 days.

(21) Appl. No.: 13/683,158

(22) Filed: Nov. 21, 2012

(65) Prior Publication Data

US 2014/0143559 A1 May 22, 2014

(51) Int. Cl.
| | |
|---|---|
| *G06F 1/28* | (2006.01) |
| *G06F 1/32* | (2006.01) |
| *A61F 2/14* | (2006.01) |
| *A61N 1/378* | (2006.01) |
| *A61N 1/36* | (2006.01) |
| *G11C 5/14* | (2006.01) |
| *G11C 11/412* | (2006.01) |

(52) U.S. Cl.
CPC .......... *G06F 1/28* (2013.01); *A61N 1/36046* (2013.01); *A61N 1/3787* (2013.01); *G06F 1/3296* (2013.01); *G11C 5/143* (2013.01); *G11C 11/4125* (2013.01); *A61F 2/14* (2013.01); *Y02B 60/1285* (2013.01)

(58) Field of Classification Search
CPC ..... G06F 1/32; G06F 1/28; G06F 1/30; G06F 11/2015; G06F 1/3296; Y02B 60/1285; A61F 2/14; A61N 1/3787

USPC ........................................................ 713/300
See application file for complete search history.

(56) References Cited

U.S. PATENT DOCUMENTS

| | | | |
|---|---|---|---|
| 4,197,850 A | 4/1980 | Schulman et al. | |
| 4,262,294 A | 4/1981 | Hara et al. | |
| 4,324,252 A | 4/1982 | Rossing et al. | |
| 4,628,933 A | 12/1986 | Michelson | |
| 4,825,350 A * | 4/1989 | Brackman, Jr. ........... | G06F 1/28 340/663 |

(Continued)

FOREIGN PATENT DOCUMENTS

| | | |
|---|---|---|
| CA | 2235216 A1 | 4/1997 |
| CA | 2235316 | 4/1997 |

(Continued)

OTHER PUBLICATIONS

Merriam-Webster. Merriam-Webster, n.d. Web. Nov. 2, 2015. <http://www.merriam-webster.com/dictionary/periodically>.*

(Continued)

*Primary Examiner* — Terrell Johnson
(74) *Attorney, Agent, or Firm* — Sughrue Mion, PLLC

(57) ABSTRACT

Power monitoring circuitry is provided, comprising a capacitor configured to receive a current, so as to charge the capacitor and a switching device, connected to the capacitor. The switching device is configured to periodically discharge the capacitor in response to receipt of a clock signal from a circuit being monitored. The power monitoring circuitry also comprises a comparator, configured to perform a comparison of a voltage developed by the capacitor with a threshold voltage, and to output an indication of a change in power supplied to the circuit in response to the comparison. Other embodiments are also described.

12 Claims, 7 Drawing Sheets

(56) References Cited

U.S. PATENT DOCUMENTS

| | | | |
|---|---|---|---|
| 4,827,261 A * | 5/1989 | Trofimenkoff | H03M 1/504 341/157 |
| 5,313,642 A * | 5/1994 | Seigel | 713/323 |
| 5,314,458 A | 5/1994 | Najafi et al. | |
| 5,712,795 A * | 1/1998 | Layman | H02J 7/0047 307/66 |
| 5,735,882 A | 4/1998 | Rottenberg et al. | |
| 5,769,875 A | 6/1998 | Peckham et al. | |
| 5,850,514 A * | 12/1998 | Gonda et al. | 714/55 |
| 6,035,236 A | 3/2000 | Jarding et al. | |
| 6,888,571 B1 | 5/2005 | Koshizuka et al. | |
| 6,976,998 B2 | 12/2005 | Rizzo et al. | |
| 7,006,873 B2 | 2/2006 | Chow et al. | |
| 7,047,080 B2 | 5/2006 | Palanker et al. | |
| 7,248,928 B2 | 7/2007 | Yagi | |
| 7,302,598 B2 | 11/2007 | Suzuki et al. | |
| 7,342,427 B1 | 3/2008 | Fensore et al. | |
| 7,831,309 B1 | 11/2010 | Humayun et al. | |
| 8,000,804 B1 | 8/2011 | Wessendorf et al. | |
| 8,150,526 B2 | 4/2012 | Gross et al. | |
| 8,428,740 B2 | 4/2013 | Gefen et al. | |
| 8,442,641 B2 | 5/2013 | Gross et al. | |
| 2001/0011844 A1 * | 8/2001 | Ernst | G06F 1/30 307/64 |
| 2002/0136034 A1 * | 9/2002 | Feldtkeller | H02M 3/33507 363/21.01 |
| 2003/0181957 A1 | 9/2003 | Greenberg | |
| 2004/0054407 A1 | 3/2004 | Tashiro et al. | |
| 2004/0082981 A1 | 4/2004 | Chow et al. | |
| 2004/0088026 A1 | 5/2004 | Chow et al. | |
| 2004/0103343 A1 * | 5/2004 | Wu | G06F 1/30 714/14 |
| 2005/0015120 A1 | 1/2005 | Seibel et al. | |
| 2005/0146954 A1 | 7/2005 | Win et al. | |
| 2005/0168569 A1 | 8/2005 | Igarashi | |
| 2006/0106432 A1 | 5/2006 | Sawan et al. | |
| 2006/0256989 A1 | 11/2006 | Olsen et al. | |
| 2006/0287688 A1 | 12/2006 | Yonezawa | |
| 2007/0222411 A1 * | 9/2007 | Cour | H01M 10/44 320/101 |
| 2008/0164762 A1 * | 7/2008 | Pecile | H02J 7/0047 307/66 |
| 2008/0294224 A1 | 11/2008 | Greenberg | |
| 2009/0002034 A1 | 1/2009 | Westendorp et al. | |
| 2009/0228069 A1 | 9/2009 | Dai et al. | |
| 2010/0087895 A1 | 4/2010 | Zhou et al. | |
| 2010/0204754 A1 | 8/2010 | Gross | |
| 2010/0249878 A1 | 9/2010 | McMahon et al. | |
| 2010/0331682 A1 | 12/2010 | Stein et al. | |
| 2011/0054583 A1 | 3/2011 | Litt et al. | |
| 2011/0172736 A1 | 7/2011 | Gefen et al. | |
| 2011/0254661 A1 | 10/2011 | Fawcett et al. | |
| 2012/0035725 A1 | 2/2012 | Gefen et al. | |
| 2012/0035726 A1 | 2/2012 | Gross | |
| 2012/0041514 A1 | 2/2012 | Gross et al. | |
| 2012/0194781 A1 | 8/2012 | Agurok | |
| 2012/0221103 A1 | 8/2012 | Liran et al. | |
| 2012/0259410 A1 | 10/2012 | Gefen et al. | |
| 2012/0268080 A1 * | 10/2012 | Jeon et al. | 320/167 |
| 2012/0283800 A1 | 11/2012 | Perryman et al. | |
| 2013/0126713 A1 | 5/2013 | Haas et al. | |
| 2013/0322462 A1 | 12/2013 | Poulsen | |
| 2014/0031931 A1 | 1/2014 | Liran et al. | |
| 2014/0047713 A1 | 2/2014 | Singh et al. | |

FOREIGN PATENT DOCUMENTS

| | | |
|---|---|---|
| CN | 1875895 | 12/2006 |
| DE | 10315397 | 10/2004 |
| DE | 10315397 A1 | 10/2004 |
| JP | 2000-350742 | 12/2000 |
| WO | WO0174444 | 10/2001 |
| WO | WO 2007/076347 | 5/2007 |
| WO | 2010/089739 A2 | 8/2010 |
| WO | 2011/086545 A2 | 7/2011 |
| WO | 2012/017426 A1 | 2/2012 |
| WO | WO 2012/114327 | 8/2012 |
| WO | 2012/153325 A2 | 11/2012 |

OTHER PUBLICATIONS

ISR and written opinion, dated Feb. 27, 2014, which issued in PCT/IB2013/060270.

Examination Report, dated Apr. 16, 2014, which issued during prosecution of EP11732733.8.

Official Action, dated Nov. 27, 2013, which issued during prosecution of JP 2011-548843.

Examination Report, dated Feb. 26, 2014, which issued during prosecution of EP10738277.2.

Extended European Search Report, dated Nov. 19, 2013, which issued during the prosecution of European Patent Application No. 11814197.7.

J.F. Rizzo, "Methods and Perceptual Thresholds for Short-Term Electrical Stimulation of Human Retina with Microelectrode Arrays", Investigative Ophthalmology and Visual Science, vol. 44, No. 12, (Dec. 1, 2003) pp. 5355-5361.

Partial International Search Report Dated Mar. 31, 2015 (previously submitted).

Partial International Search Report dated Mar. 24, 2015 (previously submitted).

Office action that issued on Feb. 5, 2015, in U.S. Appl. No. 14/199,462.

Office action that issued on Mar. 3, 2015, in U.S. Appl. No. 13/148,461.

Office action that issued on Apr. 14, 2015, in U.S. Appl. No. 14/018,850.

Invitation to pay additional fees that issued in PCT/IB2014/067417.

Invitation to pay additional fees that issued in PCT/IB2015/050224.

EP search report dated Feb. 20, 2015, that issued in EP 12782462.1.

ISR and the Written Opinion issued on Jun. 30, 2015, in PCT/IB2014/067417.

ISR and the Written Opinion issued on Jun. 30, 2015, in PCT/IB2015/050224.

Office Action that issued on Aug. 20, 2015, in U.S. Appl. No. 14/160,314.

* cited by examiner ns of the present invention, circuitry, including:
WEAK POWER SUPPLY OPERATION AND CONTROL

FIELD OF THE INVENTION

The present invention relates generally to power supplies, and specifically to operating and controlling weak power supplies and elements driven by the supplies.

BACKGROUND OF THE INVENTION

There are a number of situations where a power supply providing electrical energy to a device is only capable of producing low levels of power and/or low potential values. Typical weak power supplies having these characteristics comprise those using some type of energy harvesting from an external source, such as supplies which generate their electrical energy from ambient electromagnetic radiation or an ambient local temperature gradient. A typical achievable power of an energy harvesting power source is up to 1 W. If the external source varies, then the supply voltage generated, and/or the power delivered, may change. Such changes may affect the operation of the device being driven by the power supply.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY

There is therefore provided, in accordance with some applications of the present invention, power monitoring circuitry, including:

a capacitor configured to receive a current, so as to charge the capacitor;

a switching device, connected to the capacitor, configured to periodically discharge the capacitor in response to receipt of a clock signal from a circuit being monitored; and a comparator, configured to perform a comparison of a voltage developed by the capacitor with a threshold voltage, and to output an indication of a change in power supplied to the circuit in response to the comparison.

For some applications, the current includes a fixed charging current, and the circuitry includes a constant current generator supplying the fixed charging current.

For some applications, the threshold voltage is determined in response to a level attained by the capacitor if the capacitor is not discharged.

For some applications, the indication is output in response to the switching device ceasing to periodically discharge the capacitor.

For some applications, the circuitry includes a power supply powering the circuit, and the comparator is configured to output the indication if a voltage of the power supply is less than a lower threshold.

For some applications, the comparator is configured to output the indication if the voltage of the power supply is less than the lower threshold, the lower threshold being less than 1.5 volts.

For some applications, the comparator is configured to output the indication if the voltage of the power supply is less than the lower threshold, the lower threshold being between 0.2 volts and 0.6 volts.

There is further provided, in accordance with some applications of the present invention, circuitry, including:

a circuit including a volatile memory and an operating module configured to read from and write to the volatile memory; and a power monitoring module, configured to detect a change in power supplied to the circuit, and, in response to the change, to reduce an operating module power level supplied to the operating module while maintaining a volatile memory power level supplied to the volatile memory.

For some applications, the circuit includes a first switching circuit configured to supply power to the volatile memory and a second switching circuit configured to supply power to the operating module, and the power monitoring module is configured to operate the first and second switching circuits so as to reduce the operating module power level while maintaining the volatile memory power level.

For some applications, reducing the operating module power level includes reducing the operating module power level smoothly.

For some applications, reducing the operating module power level includes reducing the operating module power level in a stepwise fashion.

For some applications, the circuitry includes a power supply powering the circuit, and the power monitoring module is configured to detect the change if a voltage of the power supply is less than a lower threshold.

For some applications, the power monitoring module is configured to detect the change if a voltage of the power supply is less than the lower threshold, the lower threshold being less than 1.5 volts.

For some applications, the power monitoring module is configured to detect the change if the voltage of the power supply is less than the lower threshold, the lower threshold being between 0.2 volts and 0.6 volts.

There is still further provided, in accordance with some applications of the present invention, circuitry, including:

a circuit including control logic and an operating module configured to read from and write to the control logic; and a power monitoring module, configured to detect a change in power supplied to the circuit, and, in response to the change, to reduce an operating module power level supplied to the operating module while maintaining a control logic power level supplied to the control logic.

For some applications, the circuitry includes a power supply powering the circuit, and the power monitoring module is configured to detect the change if a voltage of the power supply is less than a lower threshold.

For some applications, the power monitoring module is configured to detect the change if the voltage of the power supply is less than the lower threshold, the lower threshold being less than 1.5 volts.

For some applications, the power monitoring module is configured to detect the change if the voltage of the power supply is less than the lower threshold, the lower threshold being between 0.2 volts and 0.6 volts.

There is additionally provided, in accordance with some applications of the present invention, power monitoring circuitry, including:

a first circuit element having a first performance and driven by a power supply;

a second circuit element having a second performance that emulates the first performance and is driven by the power supply so as to generate a second circuit element output; and a comparator which is configured to perform a comparison of the second circuit element output with a reference signal and to output an indication of a change in power supplied by the power supply to the first circuit element in response to the comparison.

For some applications, the second circuit element includes a replica of the first circuit element.

For some applications, the first circuit element includes a current to frequency converter.

For some applications, the second circuit element output includes a first frequency, and the reference signal includes a second frequency.

For some applications, the second circuit element includes a further current to frequency converter driven by a reference current.

For some applications, the first circuit element includes a current to voltage converter.

For some applications, the second circuit element output includes a first voltage, and the reference signal includes at least one second voltage.

For some applications, the second circuit element includes a further current to voltage converter driven by a reference current.

For some applications, the first circuit element includes a voltage to frequency converter.

For some applications, the second circuit element includes a further voltage to frequency converter.

For some applications, the comparator is configured to output the indication if a voltage of the power supply is less than a lower threshold.

For some applications, the comparator is configured to output the indication when the voltage of the power supply is less than the lower threshold, the lower threshold being less than 1.5 volts.

For some applications, the comparator is configured to output the indication if the voltage of the power supply is less than the lower threshold, the lower threshold being between 0.4 volts and 0.7 volts.

There is yet additionally provided, in accordance with some applications of the present invention, circuitry, including:

a circuit configured to supply balanced current pulses to tissue of a human body via an electrode attached to the tissue; and a power monitoring module, configured to detect a change in power supplied to the circuit, and, in response to the change, to alter operation of the circuit to ensure balancing of respective pulse charges associated with the balanced current pulses.

For some applications, the balanced current pulses include pulses which generate a net charge transfer that is smaller than 20% of the respective pulse charges.

For some applications, the balanced current pulses include pulses which generate a net charge transfer that is smaller than 5% of the respective pulse charges.

For some applications, in response to the change, the module is configured to clamp a potential of the electrode to a ground potential of the human body.

For some applications, the circuitry includes a power supply powering the circuit, and the power monitoring module is configured to detect the change if a voltage of the power supply is less than a lower threshold.

For some applications, the power monitoring module is configured to detect the change if the voltage of the power supply is less than the lower threshold, the lower threshold being less than 1.5 volts.

For some applications, the power monitoring module is configured to detect the change if the voltage of the power supply is less than the lower threshold, the lower threshold being between 0.4 volts and 0.8 volts.

There is still additionally provided, in accordance with some applications of the present invention, circuitry, including:

a circuit, including a first operating module coupled to a second operating module; and a power monitoring module, configured to detect a change in power supplied to the circuit, and, in response to the change, to wait a preset time interval, and after the preset time interval to change a first power level supplied to the first operating module while maintaining a second power level supplied to the second operating module.

For some applications, the power monitoring module is configured to change the first power level in steps.

For some applications, the change in power includes a reduction in the power supplied to the circuit, and the power monitoring module is configured to reduce the first power level supplied to the first operating module.

For some applications, the power monitoring module is configured to detect an increase in the power supplied to the circuit, to wait a further preset time interval, and after the further preset time interval to increase the first power level supplied to the first operating module while maintaining the second power level supplied to the second operating module.

For some applications, the circuitry includes a power supply powering the circuit, and the power monitoring module is configured to detect the change if a voltage of the power supply is less than a lower threshold.

For some applications, the power monitoring module is configured to detect the change if the voltage of the power supply is less than the lower threshold, the lower threshold being less than 1.5 volts.

For some applications, the power monitoring module is configured to detect the change if the voltage of the power supply is less than the lower threshold, the lower threshold being between 0.2 volts and 0.6 volts.

There is further provided, in accordance with some applications of the present invention, circuitry, including:

a configuration register, powered by a voltage, and configured to receive configuration data defining a configuration of a circuit; and error detection logic, powered by the voltage, is stored an error correction code, and which is configured to:
  perform error detection on the configuration data using the error correction code, and
  prevent the configuration register from using wrong configuration data if the voltage is low enough to affect the configuration.

For some applications, the error detection logic is configured to permit the configuration register to receive new configuration data if the voltage is equal to or above a preset limit.

For some applications, the configuration data includes at least one of an error detection value and an error correction value.

For some applications, the error detection logic is configured to perform re-loading of at least one of a default configuration code and an error correction code only if the configuration data has an error.

For some applications, the voltage low enough to affect the configuration is less than 0.5 volts.

For some applications, the voltage low enough to affect the configuration is less than 0.1 volts.

There is additionally provided, in accordance with some applications of the present invention, circuitry, including:

a volatile memory storing data and powered by a supply voltage; and a capacitor connected to the volatile memory and configured, in response to a change in the supply voltage, to store the supply voltage and subsequently discharge the supply voltage at a preset rate so as to maintain the data stored in the volatile memory for a preset time.

For some applications, the volatile memory includes a single bit memory, and the capacitor is charged from data lines of the single bit memory.

For some applications, the discharge is to at least one of the data lines.

For some applications, the supply voltage changes to a value less than 0.5 volts.

For some applications, the supply voltage changes to a value less than 0.1 volts.

There is still further provided, in accordance with some applications of the present invention, circuitry, including:

a volatile memory storing data and powered by a supply voltage; and an energy storage device connected to the volatile memory and configured, in response to a change in the supply voltage, to store the supply voltage and subsequently discharge the supply voltage at a preset rate so as to maintain the data stored in the volatile memory for a preset time.

There is still further provided, in accordance with some applications of the present invention, circuitry, including:

a plurality of electrodes, configured to be coupled to tissue of a patient;

a circuit configured to supply pulses to a first number of the electrodes; and a power monitoring module, configured to detect a change in power supplied to the circuit, and, in response to detecting the change, to reduce a number of the electrodes to which the circuit supplies pulses to a second number of electrodes, the second number being positive and lower than the first number of electrodes.

For some applications, the tissue includes retinal tissue of an eye of the patient, and the circuitry is configured to be implanted entirely within the eye of the patient.

For some applications, the circuitry further includes a power supply configured to power the circuit, and the power monitoring module is configured to detect the change if a voltage of the power supply is less than a lower threshold.

For some applications, the power monitoring module is configured to detect the change if a voltage of the power supply is less than the lower threshold, the lower threshold being less than 1.5 volts.

For some applications, the power monitoring module is configured to detect the change if the voltage of the power supply is less than the lower threshold, the lower threshold being between 0.2 volts and 0.6 volts.

For some applications, the second number of electrodes is less than 40% of the first number.

For some applications, the second number of electrodes is less than 15% of the first number.

There is yet additionally provided, in accordance with some applications of the present invention, a method for monitoring power, including:

driving a first circuit element having a first performance by a power supply;

driving a second circuit element by the power supply so as to generate a second circuit element output, the second circuit element having a second performance that emulates the first performance; and performing a comparison of the second circuit element output with a reference signal and outputting an indication of a change in power supplied by the power supply to the first circuit element in response to the comparison.

For some applications, the second circuit element includes a replica of the first circuit element.

For some applications, the first circuit element includes a current to frequency converter.

For some applications, the second circuit element output includes a first frequency, and the reference signal includes a second frequency.

For some applications, the second circuit element includes a further current to frequency converter driven by a reference current.

For some applications, the first circuit element includes a current to voltage converter.

For some applications, the second circuit element output includes a first voltage, and the reference signal includes at least one second voltage.

For some applications, the second circuit element includes a further current to voltage converter driven by a reference current.

For some applications, the first circuit element includes a voltage to frequency converter.

For some applications, the second circuit element includes a further voltage to frequency converter.

For some applications, the comparison is configured to output the indication if a voltage of the power supply is lower than a lower threshold.

For some applications, the comparison is configured to output the indication if the voltage of the power supply is lower than the lower threshold, the lower threshold being less than 1.5 volts.

For some applications, the comparison is configured to output the indication if the voltage of the power supply is lower than the lower threshold, the lower threshold being between 0.4 volts and 0.8 volts.

There is further provided, in accordance with some applications of the present invention, a method for monitoring power, including:

configuring a capacitor to receive a current, so as to charge the capacitor;

periodically discharging the capacitor in response to receipt of a clock signal from a circuit being monitored; and performing a comparison of a voltage developed by the capacitor with a threshold voltage, and outputting an indication of a change in power supplied to the circuit in response to the comparison.

For some applications, the current includes a fixed charging current supplied by a constant current generator.

For some applications, the threshold voltage is determined in response to a level attained by the capacitor if the capacitor is not discharged.

For some applications, the indication is output in response to ceasing to periodically discharge the capacitor.

For some applications, the comparison is configured to output the indication if a voltage of a power supply powering the circuit is less than a lower threshold.

For some applications, the comparison is configured to output the indication if the voltage of the power supply powering the circuit is less than the lower threshold, the lower threshold being less than 1.5 volts.

For some applications, the comparison is configured to output the indication if the voltage of the power supply powering the circuit is less than the lower threshold, the lower threshold being between 0.2 volts and 0.6 volts.

There is still additionally provided, in accordance with some applications of the present invention, a method, including:

providing a circuit including a volatile memory and an operating module configured to read from and write to the volatile memory; and detecting a change in power supplied to the circuit, and, in response to the change, reducing an operating module power level supplied to the operating module while maintaining a volatile memory power level supplied to the volatile memory.

For some applications, the circuit includes a first switching circuit configured to supply power to the volatile memory and a second switching circuit configured to supply power to the operating module, and operating the first and second switching circuits so as to reduce the operating module power level while maintaining the volatile memory power level.

For some applications, reducing the operating module power level includes reducing the operating module power level smoothly.

For some applications, reducing the operating module power level includes reducing the operating module power level in a stepwise fashion.

For some applications, the change includes a voltage of a power supply powering the circuit becoming less than a lower threshold.

For some applications, the change includes the voltage of the power supply powering the circuit becoming less than the lower threshold, the lower threshold being less than 1.5 volts.

For some applications, the change includes the voltage of the power supply powering the circuit becoming less than the lower threshold, the lower threshold being between 0.2 volts and 0.6 volts.

There is still further provided, in accordance with some applications of the present invention, a method, including:

providing a circuit including control logic and an operating module configured to read from and write to the control logic; and detecting a change in power supplied to the circuit, and, in response to the change, reducing an operating module power level supplied to the operating module while maintaining a control logic power level supplied to the control logic.

For some applications, the change includes a voltage of a power supply powering the circuit becoming less than a lower threshold.

For some applications, the change includes the voltage of the power supply powering the circuit becoming less than the lower threshold, the lower threshold being less than 1.5 volts.

For some applications, the change includes the voltage of the power supply powering the circuit becoming less than the lower threshold, the lower threshold being between 0.2 volts and 0.6 volts.

There is still further provided, in accordance with some applications of the present invention, a method, including:

configuring a circuit to supply balanced current pulses to tissue of a human body via an electrode attached to the tissue; and detecting a change in power supplied to the circuit, and, in response to the change, altering operation of the circuit to ensure balancing of respective pulse charges associated with the balanced current pulses.

For some applications, the method includes in response to the change, clamping a potential of the electrode to a potential of the human body.

For some applications, the change includes a voltage of a power supply powering the circuit becoming less than a lower threshold.

For some applications, the change includes the voltage of the power supply powering the circuit becoming less than the lower threshold, the lower threshold being less than 1.5 volts.

For some applications, the change includes the voltage of the power supply powering the circuit becoming less than the lower threshold, the lower threshold being between 0.4 volts and 0.8 volts.

There is yet additionally provided, in accordance with some applications of the present invention, a method, including:

providing a circuit including a first operating module coupled to a second operating module; and detecting a change in power supplied to the circuit, and, in response to the change, waiting a preset time interval, and after the preset time interval changing a first power level supplied to the first operating module while maintaining a second power level supplied to the second operating module.

For some applications, the method includes changing the first power level in steps.

For some applications, the change in power includes a reduction in the power supplied to the circuit, and changing the first power level includes reducing the first power level supplied to the first operating module.

For some applications, the method includes detecting an increase in the power supplied to the circuit, waiting a further preset time interval, and after the further preset time interval increasing the first power level supplied to the first operating module while maintaining the second power level supplied to the second operating module.

For some applications, the change includes a voltage of a power supply powering the circuit becoming less than a lower threshold.

For some applications, the change includes the voltage of the power supply powering the circuit becoming less than the lower threshold, the lower threshold being less than 1.5 volts.

For some applications, the change includes the voltage of the power supply powering the circuit becoming less than the lower threshold, the lower threshold being between 0.4 volts and 0.8 volts.

There is still further provided, in accordance with some applications of the present invention, a method, including:

powering a configuration register by a voltage, and configuring the register to receive configuration data defining a configuration of a circuit; and configuring error detection logic, powered by the voltage, and is stored an error correction code, to:
  perform error detection on the configuration data using the error correction code, and
  prevent the configuration register from using wrong configuration data if the voltage is low enough to affect the configuration.

For some applications, the error detection logic is configured to permit the configuration register to receive new configuration data if the voltage is equal to or above a preset limit.

For some applications, the configuration data includes an error detection value.

For some applications, the error detection logic is configured to perform re-loading of at least one of a default configuration code and an error correction code only if the configuration data has an error.

For some applications, the voltage low enough to affect the configuration is less than 0.2 volts.

For some applications, the voltage low enough to affect the configuration is less than 0.1 volts.

There is further provided, in accordance with some applications of the present invention, a method, including:

storing data in a volatile memory powered by a supply voltage; and connecting a capacitor to the volatile memory and configuring the capacitor, in response to a change in the supply voltage, to store the supply voltage and subsequently discharge the supply voltage at a preset rate so as to maintain the data stored in the volatile memory for a preset time.

For some applications, the volatile memory includes a single bit memory, and the capacitor is charged from data lines of the single bit memory.

For some applications, the discharge is to at least one of the data lines.

For some applications, the supply voltage changes to a value less than 0.2 volts.

For some applications, the supply voltage changes to a value less than 0.1 volts.

There is still further provided, in accordance with some applications of the present invention, a method, including:

storing data in a volatile memory powered by a supply voltage; and connecting an energy storage device to the volatile memory and configuring the energy storage device, in response to a change in the supply voltage, to store the supply voltage and subsequently discharge the supply voltage at a preset rate so as to maintain the data stored in the volatile memory for a preset time.

The present invention will be more fully understood from the following detailed description of the embodiments thereof, taken together with the drawings in which:

DETAILED DESCRIPTION OF EMBODIMENTS

Overview

An embodiment of the present invention comprises a power supply which is configured to deliver low amounts of electrical energy. The power supply, unless it is recharged by receiving energy from an external source, is only able to deliver the energy for short periods of time. Such a power supply is herein also termed a weak power supply. A typical weak power supply is able to deliver of the order of microwatts up to a few watts, and the voltage might drop within a fraction of a second when the external source is halted. Alternatively, a weak power supply may be characterized by unstable behavior, wherein it changes from delivering full power to delivering no power, or vice versa, within a fraction of a second. In addition to comprising a weak power supply, the embodiments described herein comprise circuitry which is able to detect when the weak power supply is unable to supply a required power level, typically when a parameter of the weak power supply is beyond a specified range of values for the parameter. The embodiments also describe different sets of apparatus which provide "graceful" solutions for handling conditions when the weak power supply is in such a "beyond-specified-range" state. Typically, the weak power supply is used in place of a battery, and the supply may derive its energy from energy harvesting elements or remote power transfer elements, such as coils which convert alternating magnetic fields to electrical signals. The weak power supply provides energy to a device which is typically an implantable medical device.

By way of example, in the following description the weak power supply is assumed to be used to power a retinal prosthesis, and the sets of apparatus providing the solutions when the power supply is in a beyond-specified-range state are assumed to be configured for a retinal prosthesis. However, use of a retinal prosthesis in the description is purely exemplary, and those having ordinary skill in the art will be able to adapt the description, mutatis mutandis, for other devices using a weak power supply, such as a cochlear prosthesis or a pacemaker.

System Description

Detection of Power Supply Out of Specification

Figure 1A:
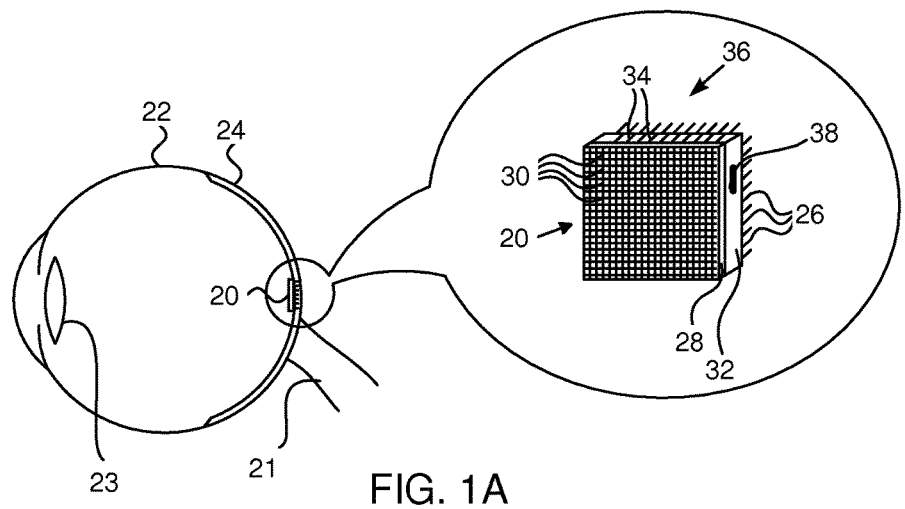
FIG. 1A is a schematic, pictorial illustration of a retinal prosthesis implanted in an eye, according to an embodiment of the present invention.

Reference is now made to FIG. 1A, which is a schematic, pictorial illustration of a retinal prosthesis 20 implanted in an eye 22, according to an embodiment of the present invention. In the pictured embodiment, which schematically illustrates a horizontal cross-section of eye 22, prosthesis 20 is implanted epiretinally, typically in proximity to an optic nerve 21, and the rear side of the prosthesis comprises an array of electrodes 26, which protrude into or otherwise contact retinal tissue 24.

Alternatively, prosthesis 20 may be implanted subretinally.

The front side of prosthesis 20 comprises an array 28 of light-sensing elements 30, typically photodiodes, which output signals in response to light that is focused onto them by optical elements of the eye, such as a lens 23. Retinal prosthesis components similar to those described herein, as well as other retinal prosthesis components, are described, for example, in PCT International Publication WO 2010/089739 and in U.S. patent application Ser. No. 12/852,218 (issued as U.S. Pat. No. 8,428,740), whose disclosures are incorporated herein by reference.

Within prosthesis 20 conversion circuitry 32 receives and processes the output signals from elements in order to generate pulses to drive electrodes 26. The circuitry typically comprises a number of generally similar channels 34, each channel 34 receiving the signal from one element 30, and driving one electrode 26. Each channel 34 uses a set 36 of circuit elements, and in the following description, where necessary, the elements of a given channel 34 and its component elements are differentiated from each other by appending a letter and/or a numeral to the channel and to the set identifying numeral. For example, in a first embodiment a given channel 34M may comprise a set 36M of elements, the set in turn comprising a trans-impedance amplifier (TIA) 36M1, a voltage to frequency converter (V2F) 36M2, and an electrode driver 36M3. In a second embodiment, a given channel 34N comprises a set of elements 36N, the set comprising a current to frequency (I2F) converter 36N1 and an electrode driver 36N2.

Functionality and properties of circuitry similar to circuitry 32 and its component elements are described in US patent application Ser. No. 13/034,516 filed Feb. 24, 2011 (issued as U.S. Pat. No. 8,571,669), which is incorporated herein by reference. As described therein, the frequency of the pulses driving electrodes similar to electrodes 26 varies from a minimum frequency typically less than 10 Hz to a maximum frequency in the order of tens or hundreds of Hz.

Elements of prosthesis 20, including array 28 and circuitry 32, are powered by a weak power supply 38, which by way of example is assumed to be incorporated into circuitry 32. A typical weak power supply is able to deliver up to hundreds of microwatts, and the voltage might drop within a fraction of a second when an external energy source is halted. Alternatively, a weak power supply may be characterized by unstable behavior, wherein it changes from delivering full power to delivering no power, or vice versa, within a fraction of a second. Such unstable behavior occurs, for example, for a power supply used in an eye that harvests light energy incident on the eye. Blinking and eye motion, for example, cause rapid reduction and return in the energy harvested.

Because of dimensional constraints on prosthesis 20, power supply 38 is usually small, and, unless it is recharged, the power supply may only be able to deliver a small amount of power to the prosthesis elements for a relatively short time. One suitable power supply, comprising an energy receiver and a voltage regulator, is described in PCT Application WO 2010/089739 referenced above. However, embodiments of the present invention may use any other suitable weak power supply, and such other supplies will be apparent to those having ordinary skill in the art.

Typically, circuitry 32 together with power supply 38 comprise one or more semiconductor chips, in which analog and/or digital circuit elements are fabricated, using methods of integrated circuit production that are known in the art. Alternatively, circuitry 32 may be fabricated at least partially using discrete circuit components, rather than integrated circuits. Array 28 of light-sensing elements 30 may be integrated into the same chip (or chips) as circuitry 32. Alternatively, array 28 may be fabricated on a separate substrate, and elements 30 may be coupled to the processing channels of circuitry 32 using methods that are known in the art.

The elements of prosthesis 20, including elements of sets 36, typically operate correctly only when the voltage supplying a given element is within an operating voltage range specified for the element. The operating voltage range for a particular element depends on the type of element, and different types of elements may be more or less constrained as to their operating voltages. For example, the specification for a digital device may provide for a relatively wide operating voltage range, whereas the specification for an analog device may indicate that the operation of the device may degrade significantly outside a relatively narrow operating range. In addition, the valid operating range for any particular device may be a function of how the device is implemented and/or of the function being performed by the device. For example, a digital logic device using CMOS (complementary metal-oxide-semiconductor) technology typically has a wider operating voltage range than an analog circuit.

Figure 1B:
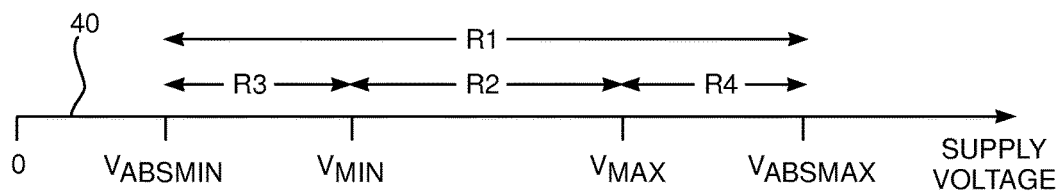
FIG. 1B is a schematic number line illustrating different voltage ranges for an element in the retinal prosthesis, according to an embodiment of the present invention.

FIG. 1B is a schematic number line 40 illustrating different voltage ranges for an element in prosthesis 20, according to an embodiment of the present invention. Number line 40 plots the element supply voltage, i.e., the voltage between the two voltage rails supplying electrical power to the element. On receipt of an appropriate voltage level, typically a few tenths of a volt, the element is configured to perform according to a prescribed specification. A lowest voltage $V_{ABSMIN}$ is a low voltage below which the element performs none of the functions of the specification. A highest voltage $V_{ABSMAX}$ is a high voltage above which the element also performs none of the functions. (Subjecting the element to voltages above $V_{ABSMAX}$ may irreversibly damage the element, while subjecting the element to voltages below $V_{ABSMIN}$ typically causes no permanent damage.)

Within a voltage range R1, between $V_{ABSMIN}$ and $V_{ABSMAX}$ is a smaller voltage range R2, between a lower voltage $V_{MIN}$ and a higher voltage $V_{MAX}$. In range R2 the element is able to correctly operate according to the specification of the element. In the description herein, if an element is not within its range R2, it may be referred to as being out of specification.

Two further ranges may be considered for the element: a range R3 between $V_{ABSMIN}$ and $V_{MIN}$, and a range R4 between $V_{MAX}$ and $V_{ABSMAX}$. Within ranges R3 and R4 the element typically operates partially according to the element specification. For an analog device the partial operation may typically be manifested as a reduced dynamic range and/or introduction of distortion and/or clipping into the output of the device. For a digital device the partial operation may manifest itself as unstable signals. In some cases, range R4 does not exist, since the R2 range is defined up to the maximum supplied voltage $V_{ABSMAX}$.

It will be understood that for any given element the range bounds described above, $V_{ABSMIN}$, $V_{ABSMAX}$, $V_{MIN}$ and $V_{MAX}$, may be adaptive, i.e., they may depend on a number of parameters applicable to the element. The parameters include, but are not limited to, a temperature at which the element is operating, an impedance of a component driving the element, and an impedance of a component being driven by the element. The parameters also include functions required of the element, such as whether the element is quiescent, is providing a clock signal of a given frequency, or is amplifying an incoming signal. Other adaptive parameters affecting the range bounds will be apparent to those having ordinary skill in the art, and all such parameters are included in the scope of the present invention.

Embodiments of the present invention detect if an element is within partial operating ranges such as those described above, e.g., within ranges R3 or R4. The embodiments also provide solutions for handling the reduced operating characteristics of an element when it is within such partial operating ranges.

A typical range for $V_{ABSMIN}$ is approximately 0.05V to approximately 0.3V; a typical range for $V_{MIN}$ is approximately 0.2V to approximately 0.7V; and a typical range for $V_{MAX}$ is approximately 0.7V to approximately 1.5V. $V_{ABSMAX}$ is greater than or equal to the respective value of $V_{MAX}$, and is bounded by the limitations of the voltage of the devices of the selected process technology. In a first disclosed embodiment values of $V_{ABSMIN}$, $V_{MIN}$, and $V_{MAX}$ are respectively approximately equal to 0.2V, 0.4V, and 1.5V; in a second disclosed embodiment $V_{ABSMIN}$, $V_{MIN}$, and $V_{MAX}$ are respectively approximately equal to 0.1V, 0.7V, and 1.1V, and in a third disclosed embodiment values of $V_{ABSMIN}$, $V_{MIN}$, and $V_{MAX}$ are respectively approximately equal to 0.1V, 0.4V, and 1.5V. Other sets of values of $V_{ABSMIN}$, $V_{MIN}$, and $V_{MAX}$ will be apparent to those having ordinary skill in the art, and all such sets are assumed to be within the scope of the present invention.

The description above referring to detecting if an element is within a partial operating range, and providing solutions for such cases, may be applied, mutatis mutandis, to a group of such elements, or to a device comprising a number of separate elements, such as prosthesis 20 or power supply 38. All such applications are considered to be within the scope of the present invention.

Figure 2A:
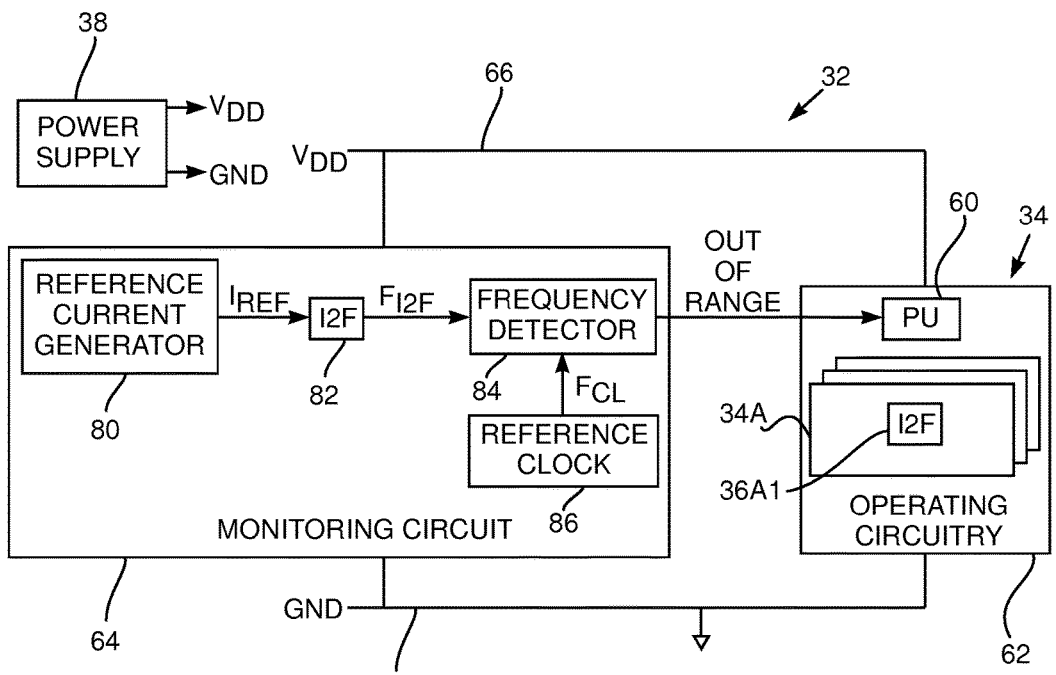
FIG. 2A is a block diagram that schematically illustrates conversion circuitry, according to an embodiment of the present invention.

FIG. 2A is a block diagram that schematically illustrates conversion circuitry 32, according to an embodiment of the present invention. Conversion circuitry comprises channels 34, each given channel 34A comprising an I2F converter 36A1. A processing unit (PU) controls the operation of channels 34, and the combination of PU 60 and channels 34 is also referred to herein as operating circuitry 62. Power supply 38 supplies power to operating circuitry 62.

Conversion circuitry 32 comprises a power supply monitoring circuit 64, which is itself powered by power supply 38 and which monitors the voltage difference between a power rail 66, supplying a voltage $V_{DD}$, and a ground (GND) rail 68 of the power supply. The monitoring circuit measures the voltage difference between the two rails, and provides one or more out-of-range levels to PU according to a difference from a preset range of values within which operating circuitry 62 can operate correctly.

For the first disclosed embodiment referred to above, monitoring circuit 64 may check that the voltage difference between the power and ground rails of power supply 38 lies typically between 0.4V, corresponding to $V_{MIN}$, and 1.5V, corresponding typically to $V_{MAX}$. If the difference is less than 0.4V, a low out-of-range level is output, and if the difference is greater than 1.5V a high out-of-range level is output.

Monitoring circuit 64 may perform a similar check for other voltages. For example, for the second disclosed embodiment referred to above, the circuit may check that the voltage difference between the rails of power supply 38 lies between about 0.7V, $V_{MIN}$, and about 1.1V, $V_{MAX}$. If in this case, the difference is less than 0.7V the low out-of-range level is output, and if the difference is greater than 1.1V the high out-of-range level is output.

In some embodiments, an out-of-range level is output as a threshold-crossing indication to PU 60 if a voltage of the power supply is less than a lower threshold. In a further disclosed embodiment the lower threshold is set to be less than 1.5 volts. In an alternative further disclosed embodiment, the lower threshold is in a range of 0.4 volts to 0.7 volts, or in a range of 0.4 volts to 0.8 volts.

Figure 2B:
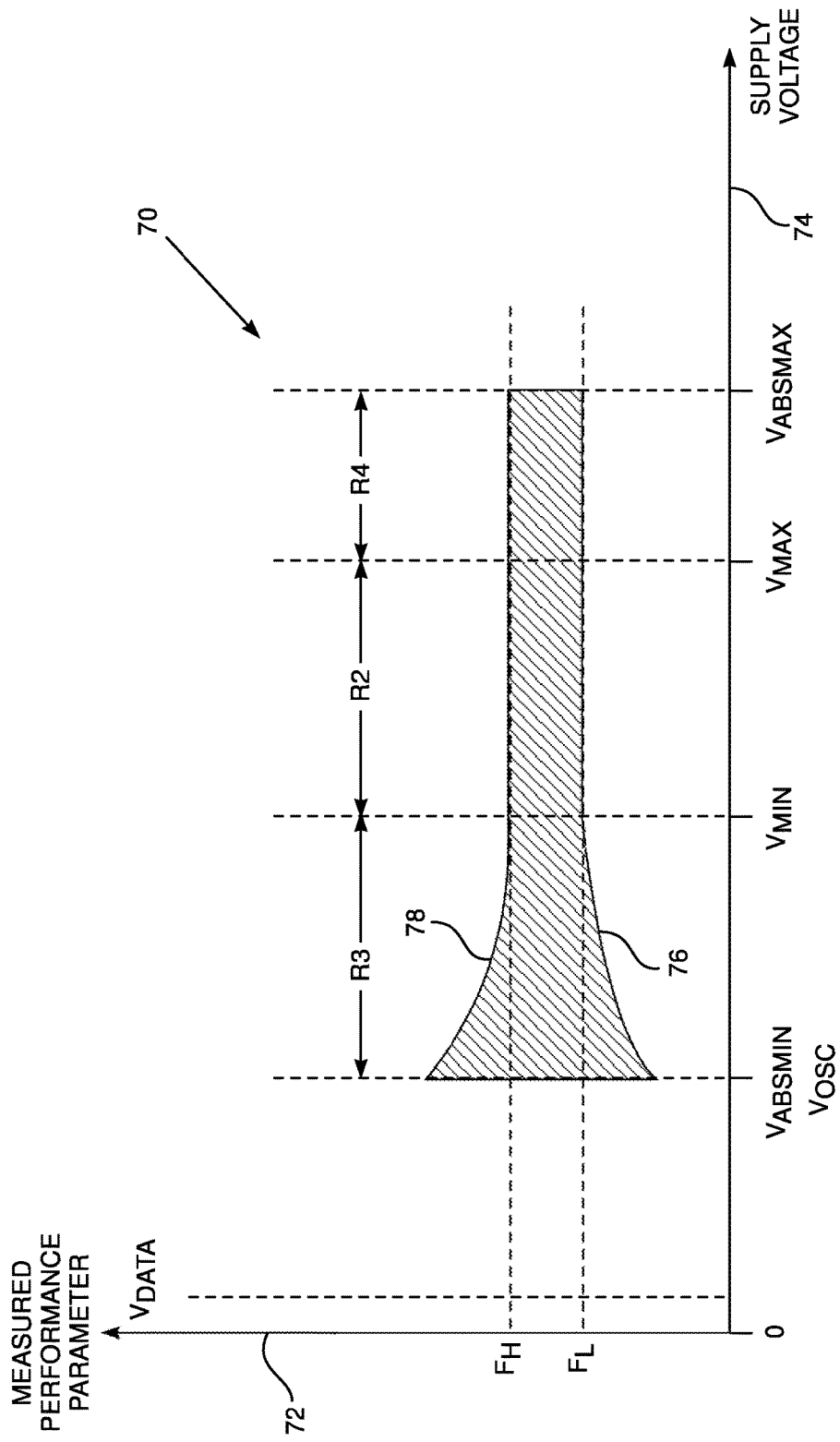
FIG. 2B is a schematic graph of the performance of a current to frequency converter, according to an embodiment of the present invention.

FIG. 2B is a schematic graph 70 of the performance of a system component, showing a measured performance parameter of the component, according to an embodiment of the present invention. By way of illustration and not limitation, the component may be I2F converter 36A1, as described in the following example. Graph 70 is derived from the specification of the I2F converter, and plots frequencies generated by the converter, on a vertical axis 72, vs. supply voltages applied to the converter on a horizontal axis 74. Axis 74 is generally similar to number line 40 (FIG. 1B), so that supply voltages $V_{ABSMIN}$, $V_{ABSMAX}$, $V_{MIN}$, and $V_{MAX}$, as well as ranges R2, R3, and R4, are as defined above with respect to line 40, and apply to I2F converter 36A1. Graph 70 illustrates other parameters that are relevant to the performance of the I2F converter.

Within the bounds defined by $V_{MIN}$ and $V_{MAX}$, i.e., in range R2 wherein the voltage powering the converter enables the converter to operate to its complete specification, the frequency output by the converter is able to vary between a low frequency $F_L$ and a high frequency $F_H$ for given respective low and high currents received by the converter. It is noted that another parameter besides frequency may be used, as well.

As the supply voltage decreases and enters range R3, the low and high frequencies generated by the converter (for the given received currents) change, as shown by lines 76 and 78.

Referring back to the description of prosthesis 20 and to FIG. 1A, there is a minimum pulse frequency, typically of a few Hertz, and in a disclosed embodiment less than 10 Hz. There is also a maximum pulse frequency, typically up to a few hundred Hertz and in a disclosed embodiment greater than 200 Hz. The pulse frequency drives electrodes 26.

The voltage $V_{DATA}$, which is lower than $V_{ABSMIN}$, is described below, and is shown on graph 70 for simplicity. Voltage $V_{OSC}$, also shown on graph 70 and described below, is typically equal to $V_{ABSMIN}$, but may be lower than $V_{ABSMIN}$. (It is noted that $V_{OSC}$ is shown in FIG. 2B, although in general the figure is intended to apply to any monitored parameter, and not only to frequency.)

Returning to FIG. 2A, monitoring circuit 64 comprises a reference current generator 80 which supplies a preset fixed reference current $I_{REF}$ to a circuit element 82 (e.g., $I_{REF}$ representing the minimum current input to the I2F converter for complying with the specification requirements). Element 82 is assumed, by way of example, to comprise an I2F converter which is typically, but not necessarily, a replica of I2F converter 36A1. Element 82, herein also referred to as I2F converter 82, generally emulates the performance and transfer function of converter 36A1. In response to reference current $I_{REF}$, converter 82 generates a frequency $F_{I2F}$, according to the transfer function of the converter. Frequency $F_{I2F}$ is a first input of a frequency detector 84.

Circuit 64 also comprises a reference clock 86, which provides a reference clock frequency $F_{CL}$ as a second input to the frequency detector. Clock 86 is typically configured to be more stable than the frequency generated by the combination of current generator 80 and I2F converter 82. Using frequency $F_{CL}$ as a reference, detector 84 determines if frequency $F_{I2F}$ is within preset acceptable limits, and so effectively checks if the voltage applied to I2F converter 82 from power supply 38 is within range R2 (FIG. 2B). If frequency $F_{I2F}$ is within the preset limits, detector 84 is configured to provide a signal to PU 60 indicating that the voltage from the power supply enables I2F converter 82 to operate according to the complete specification of the converter. Alternatively, the detector provides no signal, which provides the same indication to the processing unit.

If frequency $F_{I2F}$ is outside the preset limits, detector 84 is configured to provide an "out-of-range" signal to PU 60, indicating that the voltage provided to I2F converter 82 is in range R3, so that the converter is out of specification but is able to partially operate. In some embodiments, detector 84 is configured to provide respective different out-of-range signals, according to sub-ranges of range R3.

Typically, except for I2F converter 82, the components of monitoring circuit 64, i.e., generator 80, detector 84, and clock 86 are configured to operate acceptably at voltages below $V_{ABSMIN}$. For example, clock 86 is able to provide its clock signals so long as power supply 38 generates a voltage greater than or equal to $V_{ABSMIN}$. A voltage $V_{DATA}$, which is less than $V_{ABSMIN}$, is a voltage below which data stored in volatile memory elements of prosthesis 20 may be lost.

As explained above, monitoring circuit 64 may evaluate the performance of a replica of an element of one of channels 34 (in operating circuitry 62) in order to determine a range of the voltage supplied by power supply 38 to the operating circuitry.

Figure 3:
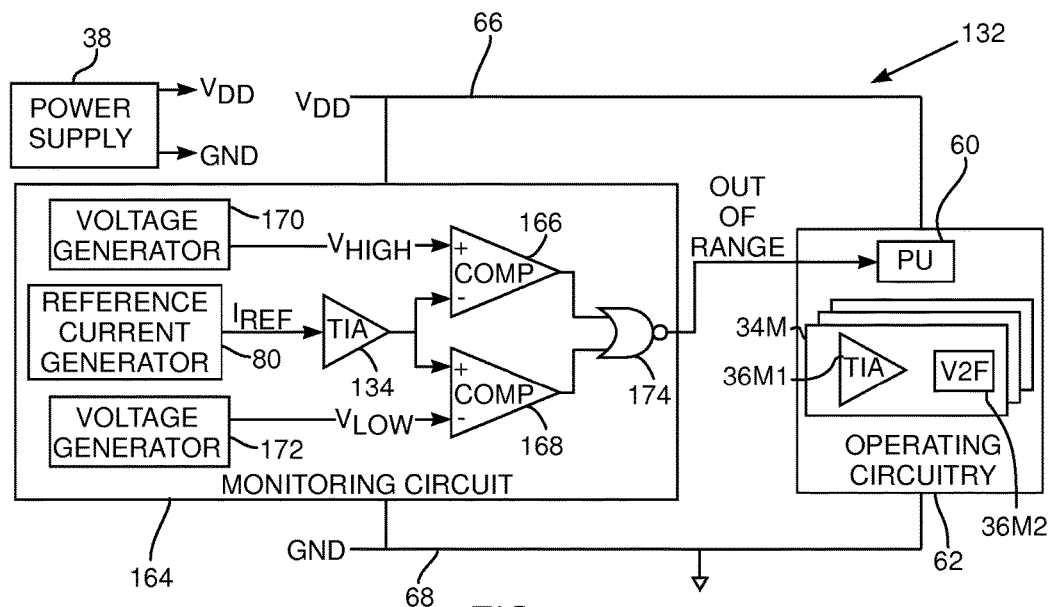
FIG. 3 is a block diagram that schematically illustrates alternative conversion circuitry, according to an embodiment of the present invention.

FIG. 3 is a block diagram that schematically illustrates conversion circuitry 132, according to an alternative embodiment of the present invention. Apart from the differences described below, the operation of circuitry 132 is generally similar to that of circuitry 32 (FIGS. 2A and 2B), and elements indicated by the same reference numerals in both circuitry 32 and 132 are generally similar in construction and in operation.

In the alternative embodiment illustrated in FIG. 3, respective sets 36 of channels 34 comprise TIAs and V2Fs, so that set 36M of elements of a particular channel 34M comprises TIA 36M1 and V2F 36M2. (The TIA and V2F of each specific channel may be connected in series so as to have generally the same performance as an I2F.)

In circuitry 132, a monitoring circuit 164 performs a similar function to that of monitoring circuit 64, in order to evaluate the voltage supplied by power supply 38. However, monitoring circuit 164 assesses the performance of an element 134. Element 134 is configured to have a performance that emulates that of TIA 36M1. Element 134 is typically, although not necessarily, a replica of TIA 36M1, and the element is herein also referred to as TIA 134. In order to make its assessment, circuit 164 comprises two similar comparators 166 and 168, as well as reference voltage generators 170 and 172. Generator 170 outputs a predetermined fixed constant voltage $V_{HIGH}$, and generator 172 outputs a predetermined fixed constant voltage $V_{LOW}$; $V_{HIGH} > V_{LOW}$. The values of $V_{HIGH}$ and $V_{LOW}$ are selected so that, as described hereinbelow, an output of a NOR gate 174 is indicative as to whether the voltage supplied by power supply 38 to TIA 134 is within limits that allow the TIA to operate correctly.

Comparator 166, which is used only if $V_{ABSMAX}$ 22 $V_{HIGH}$, receives constant voltage $V_{HIGH}$ and an output $V_O$ from TIA 134, and compares the two inputs. If $V_O > V_{HIGH}$, the comparator outputs a '1'. If $V_O \leq V_{HIGH}$ the comparator outputs a '0'.

Comparator 168 receives constant voltage $V_{LOW}$ and output $V_O$, and compares the two inputs. If $V_O < V_{LOW}$, the comparator outputs a '1'. If $V_O \geq V_{LOW}$, comparator 168 outputs a '0'.

When $V_{ABSMAX} > V_{HIGH}$, the outputs of the two comparators are input to NOR gate 174. If either $V_O < V_{LOW}$ or $V_O > V_{HIGH}$, then NOR gate 174 outputs a '0'. PU 60 is configured to interpret a '0' from the NOR gate as an out-of-range indication, i.e., that the voltage supplied to TIA 134 is within a range, corresponding to one of ranges R3 and R4 (FIG. 2B), wherein TIA 134 operates partially according to its specification. Those having ordinary skill in the art will be able to adapt the circuit of FIG. 3 to monitor the output of TIA with respect to just one bound $V_{LOW}$ or $V_{HIGH}$, rather than the two bounds described above.

When $V_{ABSMAX} = V_{HIGH}$, comparator 166 is not used, and NOR gate 174 is replaced by an inverter, or the polarity of comparator 168 is inverted.

As described above with reference to monitoring circuit 64, in the embodiment illustrated in FIG. 3, circuit 164 evaluates the performance of a replica of an element, herein a TIA, of one of channels 34 in operating circuitry 62 in order to determine a range of the voltage supplied by power supply 38 to the operating circuitry.

Alternatively, circuit 164 may be reconfigured to evaluate the performance of a replica of a different element, such as V2F converter 36M2. The reconfiguration, mutatis mutandis, is generally as described for monitoring circuit 64 (FIG. 2A), except that current generator 80 is replaced by a voltage source, and I2F converter 82 is replaced by a V2F converter.

Figure 4A:
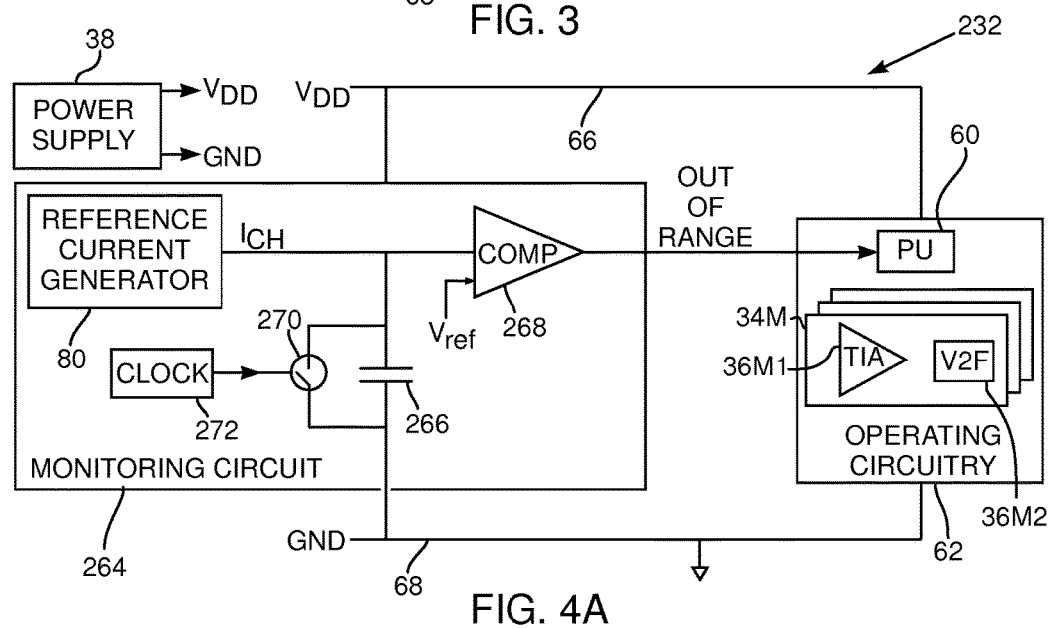
FIG. 4A is a block diagram that schematically illustrates further alternative conversion circuitry, according to an embodiment of the present invention.
Figures 4B, 4C:
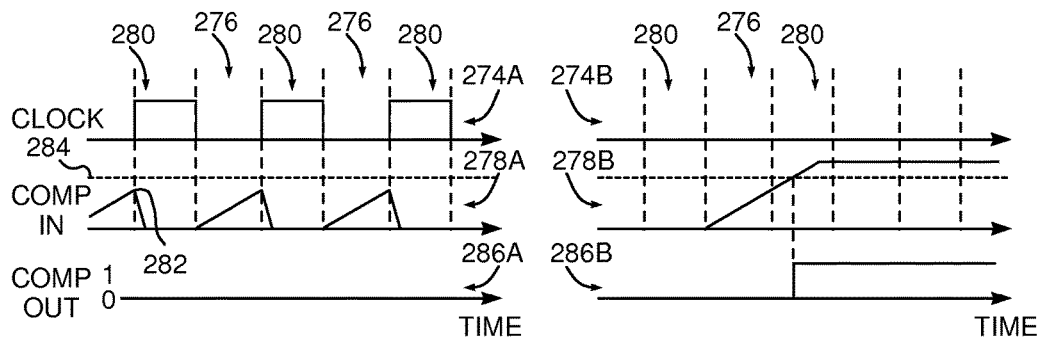
FIGS. 4B and 4C are graphs illustrating the operation of the circuitry of FIG. 4A, according to embodiments of the present invention.

FIG. 4A is a block diagram that schematically illustrates conversion circuitry 232, and FIGS. 4B and 4C are graphs illustrating the operation of the circuitry, according to alternative embodiments of the present invention. The purpose of this circuitry is to monitor the operation of the oscillator that generates clock pulses from a clock circuit 272, and to verify that it is within a specific limit. Apart from the differences described below, the operation of circuitry 232 is generally similar to that of circuitry 132 (FIG. 3), and elements indicated by the same reference numerals in both circuitry 132 and 232 are generally similar in construction and in operation. Thus, for example, circuitry 232 may be used to monitor voltage levels corresponding to those of the first, second, and third disclosed embodiments referred to above.

In a power supply monitoring circuit 264, reference current generator 80 is configured as a current generator which provides a fixed current $I_{CH}$ to charge a capacitor 266. In some embodiments generator 80 comprises a resistor. The generator is connected to a first conductor or plate of the capacitor, and a second plate of the capacitor is connected to ground rail 68. A comparator 268 is connected to the first plate of capacitor 266.

A switch 270 is connected across capacitor 266 in a configuration that enables the switch to short the capacitor when the switch is closed. In one embodiment, switch 270 is an NMOS transistor having its source connected to the first plate of the capacitor and its drain connected to the capacitor second plate.

FIG. 4B illustrates graphs of the behavior of circuitry 232 when power supply 38 is generating its specified voltage levels ($V_{DD}$ and GND). As shown in FIG. 4B, a clock circuit 272 produces clock pulses, illustrated by a graph 274A, and the circuit is connected so that the pulses drive the gate of switch 270. In periods 276 when there are no clock pulses, switch 270 is open. Thus, in periods 276 capacitor 266 charges up so that, as shown by a graph 278A of the voltage input to comparator 268, the voltage on the comparator increases. The comparator typically has some internal switching threshold, causing the output to change when the input exceeds this threshold. An example of such a comparator is a simple CMOS inverter. Implementing the comparator with hysteresis is an optional embodiment of comparator 268.

In periods 280 when there are clock pulses, switch 270 is closed and so acts as a short circuit. Thus, in periods 280, capacitor 266 discharges, i.e., the capacitor is periodically discharged. In these periods the voltage on comparator 268 falls to a value close to zero.

Graph 278A illustrates that the input voltage to the comparator periodically reaches a maximum level 282, then falls to zero. In embodiments of the present invention, comparator 268 is configured to compare its received input voltage with a preset voltage level 284, corresponding to $V_{ref}$ in FIG. 4A, greater than maximum level 282. If maximum 282 is less than level 284, then the comparator outputs a '0' to PU 60. This is illustrated in a graph 286A of the output of comparator, showing that the comparator output is '0'.

FIG. 4C illustrates graphs of the behavior of circuitry 232 when power supply 38 is not generating its specified voltage levels, i.e., the supply is out of specification so that clock circuit 272 has ceased to provide pulses, as shown in a graph 274B. The cessation of pulses prevents transistor 270 from discharging the capacitor. The capacitor thus charges to a voltage higher than preset voltage 284, as shown in a graph 278B. At the time when the capacitor reaches this higher voltage, the comparator outputs a '1', as shown in a graph 286B. PU 60 is configured to interpret the '1' as an out-of-range signal. The level '1' output by the comparator continues as long as clock 272 does not generate clock pulses.

FIGS. 4B and 4C illustrate two extremes of a range of possible states of circuitry 232—a first state wherein power supply 38 supplies power to clock circuit 272 so that comparator 268 never outputs an out-of-range signal, and a second state wherein the comparator outputs an out-of-range signal continuously. It will be understood that if the clock pulses generated by clock circuit 272 change from those described above, for example, if the pulse frequency decreases and/or if the period when there is no pulse increases, the comparator may output an out-of-range signal intermittently. Such an intermittent situation may occur if power supply 38 supplies a voltage less than that specified, but greater than zero, to clock circuit 272. Typically, PU 60 is configured to interpret an intermittent out-of-range signal as indicative of power supply 38 being in range R3 (FIG. 2B).

As for circuitry 232, in some embodiments of circuitry 232 an out-of-range level is output as a threshold-crossing indication to PU 60 if a voltage of the power supply is less than a lower threshold, which is typically less than 1.5 volts. For example, the lower threshold may be set to be within a range of 0.2 volts to 0.6 volts.

Circuitry Operation when the Power Supply is Out of Specification

Figure 5:
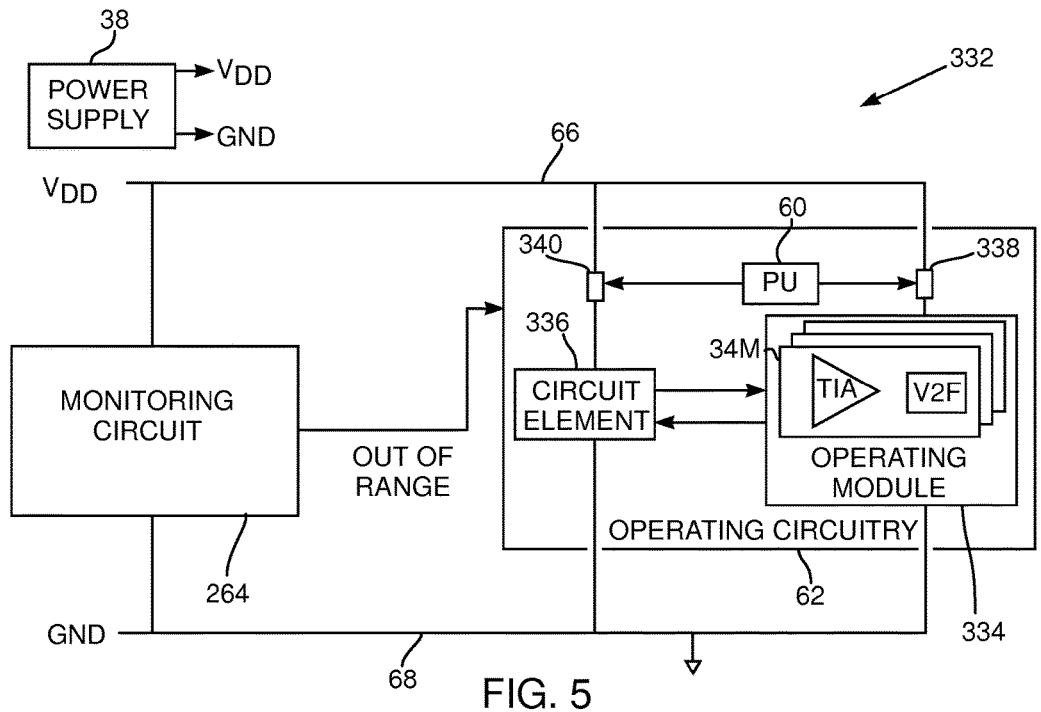
FIG. 5 is a block diagram that schematically illustrates yet further alternative conversion circuitry, according to an embodiment of the present invention.

FIG. 5 is a block diagram that schematically illustrates conversion circuitry 332, according to an embodiment of the present invention. Apart from the differences described below, the operation of circuitry 332 is generally similar to that of circuitry 232 (FIGS. 4A-C), and elements indicated by the same reference numerals in both circuitry 232 and 332 are generally similar in construction and in operation. For clarity, in the description of circuitry 332, the circuitry is assumed by way of example to comprise monitoring circuit 264. Those having ordinary skill in the art will be able to adapt the description, mutatis mutandis, for other circuits monitoring power supply 38.

For simplicity, channels 34 are assumed to be grouped as an operating module 334. During operation of circuitry 332, the channels of the module are able to communicate with a circuit element 336. Hereinbelow, except as otherwise indicated, element 336 is assumed to comprise a volatile memory, so that the channels read from and write to volatile memory 336. In some embodiments, at least part of volatile memory 336 is incorporated into channels 34. Operating circuitry 62 is configured so that module 334 and memory 336 independently receive power from power supply 38, via respective switching circuits 338 and 340, which each typically comprise one or more transistors. Switching circuits 338 and 340 are controlled by PU 60.

If PU 60 receives an out-of-range signal from monitoring circuit 264, the processing unit may be configured to reduce or cut off the power to the channels of module 334, while maintaining the power to volatile memory 336, using switching circuits 338 and 340, or in an alternative implementation, by stopping the switching or DC power consumption of some or all of the operation circuits. Such a procedure reduces or completely stops the operation of the channels of module 334, while maintaining the data in the volatile memory.

Typically, as described above, the out-of-range signal is output as a threshold-crossing indication to PU 60 if a voltage of the power supply is less than a lower threshold, which is typically less than 1.5 volts. For example, the lower threshold may be a value that is between 0.2 volts and 0.6 volts.

In one embodiment the reduction in the power level is performed smoothly. In an alternative embodiment, the reduction in the power level is performed in a stepwise fashion. Typically, the reduction in power level is configured to avoid instability and/or ringing in a circuit being energized by the power supply.

By controlling which elements of circuitry 332 continue to receive adequate power (in this case the volatile memory) when the available power is reduced, typically when the voltage driving circuitry 332 reduces to a few tenths of a volt, the processing unit ensures that when the available power enables the channels of module 334 to resume full operation, the data in the memory is effectively instantly available for the operation of the channels.

Thus, in circuitry 332, PU 60 and monitoring circuit 264 effectively act together as a power monitoring module that maintains the data in memory 336 valid even under reduced power situations.

In an alternative embodiment, rather than circuit element 336 comprising a volatile memory, the element comprises other circuitry such as control logic.

Figure 6A:
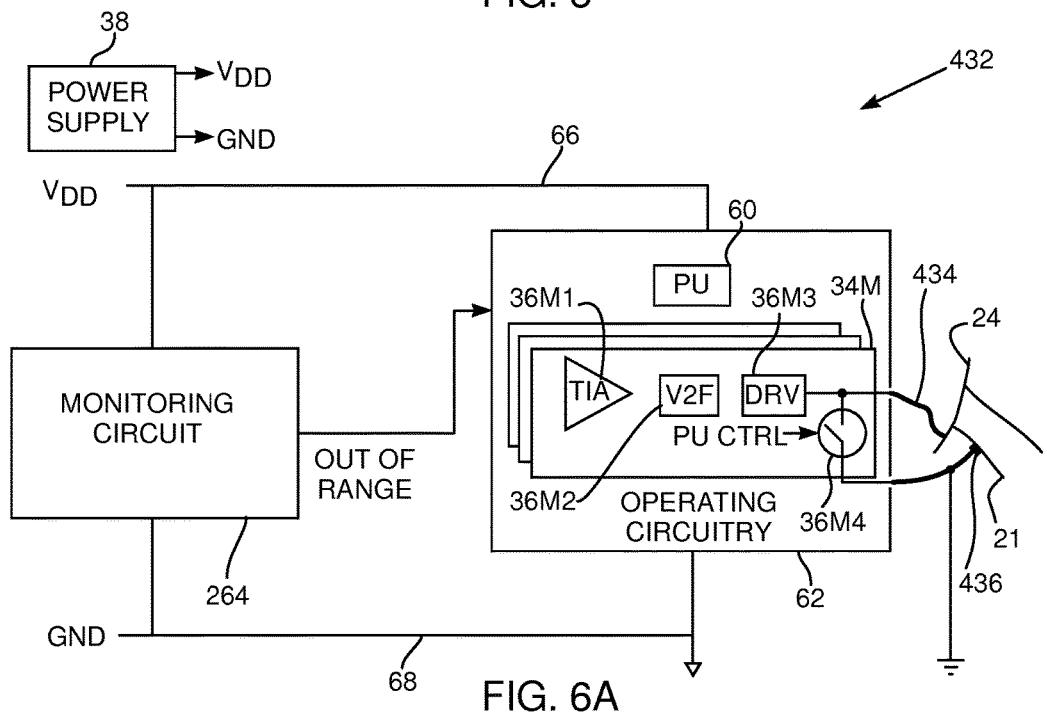
FIG. 6A is a block diagram that schematically illustrates disclosed conversion circuitry, according to an embodiment of the present invention.
Figure 6B:
FIG. 6B illustrates examples of voltage vs. time graphs of pulses used by the circuitry of FIG. 6A, according to an embodiment of the present invention.

FIG. 6A is a block diagram that schematically illustrates conversion circuitry 432, and FIG. 6B illustrates examples of voltage vs. time graphs of current pulses used by the circuitry, according to embodiments of the present invention. Apart from the differences described below, the operation of circuitry 432 is generally similar to that of circuitry 232 (FIGS. 4A-C), and elements indicated by the same reference numerals in both circuitry 232 and 432 are generally similar in construction and in operation.

During typical operating conditions, current pulses delivered by channels 34 to their respective electrodes are configured to be balanced, i.e. to comprise pulses which over a period of time generate no net charge transfer. FIG. 6B illustrates examples of voltage vs. time graphs of balanced pulses. If power is reduced to channels 34 by power supply 38 operating out of its specification, then, unless there are safeguards in place, the channels may deliver unbalanced pulses, i.e., pulses having a net charge transfer, to their electrodes. Such unbalanced pulses may, inter alia, induce electrochemical corrosion, leading to dissolution of the metal of the electrodes. Circuitry 432 safeguards against the delivery of unbalanced pulses.

Each channel 34 is assumed to have a respective electrode driver, so that channel 34M has a driver 36M3 in its set of elements 36M. Driver 36M3 is connected to an electrode 434 which, by way of example, is assumed to be coupled to retinal tissue 24 and to be in proximity to optic nerve 21 (FIG. 1).

Each channel 34 also typically comprises a switch which is operated by PU 60 (or by an alternative power reduction circuit), and which is normally closed and opens by PU 60 only when driver 36M3 is active. In a power shortage situation switch 36M4 may be closed at all times by a signal from PU 60 to ensure no imbalanced pulses are delivered. In its closed state, switch 36M4 connects electrode 434 to a local, human body, ground electrode 436. By way of example, ground electrode 436 is assumed to be connected to the outside of the optic nerve, which acts as a local ground. However, electrode 436 may be connected to any other convenient location which is able to act as a local human body ground.

Alternatively or additionally, in some embodiments, electrode 436 may be connected to ground rail 68. If PU 60 receives an out-of-range signal from monitoring circuit 264, the processing unit may be configured to transmit a PU CTRL signal to one or more channels 34. The out-of-range signal may be output as a threshold-crossing indication to PU 60 if a voltage of the power supply is less than a lower threshold, which is typically less than 1.5 volts. For example, the lower threshold may be set to be within a range of 0.4 volts to 0.8 volts.

Receipt of the PU CTRL causes the switch of the respective channel to close, so clamping the potential of the electrode connected to the channel to the local ground potential. In the example illustrated in FIG. 6A, signal PU CTRL cause electrode 434 to be clamped to the local ground.

By clamping electrodes to the local ground potential, circuitry 432 prevents the possibility of unbalanced pulses being transmitted to the electrodes.

Alternatively, instead of the channels comprising a switch such as switch 36M4, the channels may be configured to have power down circuitry that reduces the current consumption of the module significantly. In one embodiment, the reduced current consumption maintains a reduced number of active channels at, for example, less than 40% of the total number of channels. In an embodiment the reduced current consumption maintains a reduced number of active channels at less than 15% of the total number of channels. In this manner, for example, even though there may be insufficient power available to drive all of the electrodes of a retinal prosthesis to apply pulses to a patient's retina, at least a small number of the electrodes continue to operate and apply pulses to the retina.

Figure 7:
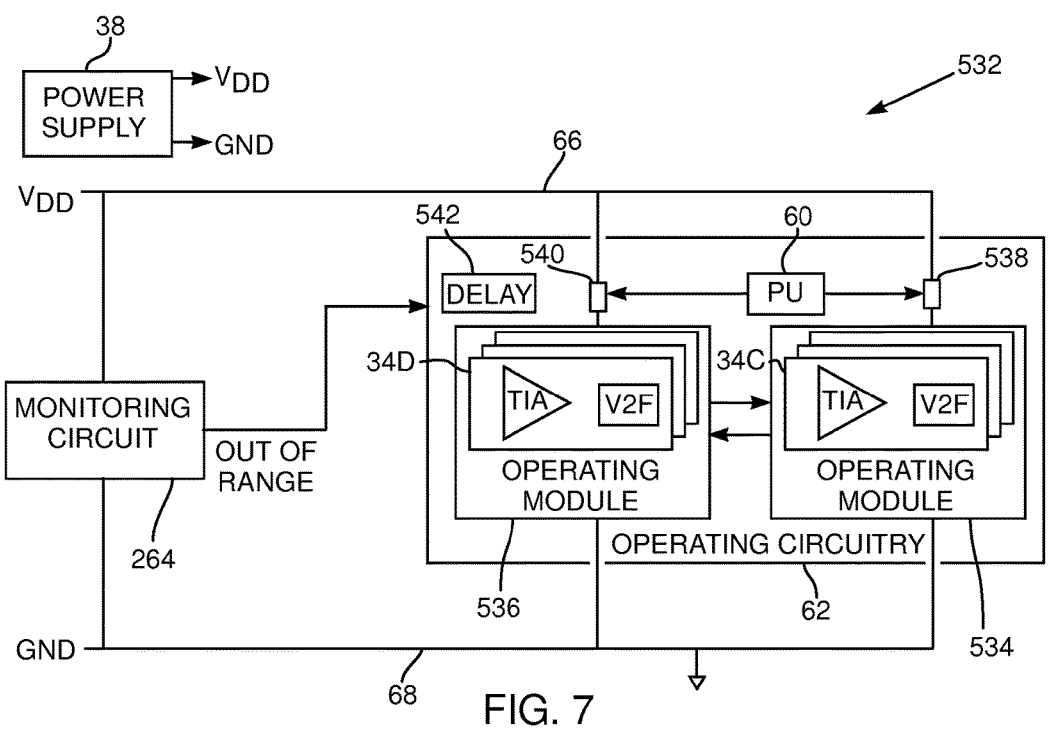
FIG. 7 is a block diagram that schematically illustrates alternative disclosed conversion circuitry, according to an embodiment of the present invention.

FIG. 7 is a block diagram that schematically illustrates conversion circuitry 532, according to an embodiment of the present invention. Apart from the differences described below, the operation of circuitry 532 is generally similar to that of circuitry 232 (FIGS. 4A-C), and elements indicated by the same reference numerals in both circuitry 232 and 532 are generally similar in construction and in operation.

If power is reduced to circuitry 532 by power supply going out of specification, some components or circuits of the circuitry may oscillate in behavior. For example, a clock circuit may cease generating pulses due to a lowered voltage from power supply 38. However, because of the reduced current demand from the clock circuit, the voltage provided by supply 38 may then rise. Such an increase in voltage might cause the oscillator to re-start oscillating, which will increase the current and drop the supply voltage. This behavior might repeat again and again, causing oscillations of the power supply voltage.

In circuitry 532, channels 34 of operating circuitry are assumed to be divided into two sets of channel operating modules: a first operating module set 534 having channels such as channel 34C, and a second operating module set 536 having channels such as channel 34D. The two modules are controlled by PU 60, so are effectively coupled together. Each operating module is assumed to be powered separately, via respective power controls 538 and 540 which are operated by PU 60, from power supply 38. A division of channels in such a manner may be implemented for central and peripheral light sensing elements 30 and their respective channels 34 (FIG. 1). By way of example, in the case of power supply providing a voltage which is out of specification, first set 534 is assumed to have its power reduced by PU 60 before second set 536. However, the division into two operating modules of operating circuitry 62 is by way of example, and those having ordinary skill in the art will be able to adapt the description herein, mutatis mutandis, for the division of circuitry, such as conversion circuitry 532, into other operating modules powered separately by power supply 38.

Circuitry 62 typically comprises a time delay module 542 which incorporates a preset time interval. On receipt of an out-of-range signal from monitoring circuit 264, indicating that the voltage supplied by power supply 38 is out of specification, PU 60 accesses the time delay module to retrieve the preset time interval. The processing unit waits the preset time interval before activating power control 538 to reduce the power to module 534, but maintains the power to module 536, via control 540, during the time interval and after the interval has elapsed. The same mechanism may be applied when the out-of-range signal is de-asserted, enabling stabilization time during power-up. Thus, for example, after the de-assertion of the out-of-range signal, the processing unit may wait a second preset time interval, prior to activating power control 538 to increase power to module 534. (The second time interval is typically but not necessarily longer than the preset time interval that precedes power reduction to module 534.)

The out-of-range signal may be output as a threshold-crossing indication to the processing unit if a voltage of the power supply is less than a lower threshold, which is typically less than 1.5 volts. For example, the lower threshold may be between 0.2 volts to 0.6 volts, or 0.4 volts to 0.8 volts.

In some embodiments, PU 60 may be configured to reduce the power to power module 534 gradually in steps. Typically in such embodiments, module 534 may be divided into subsets of channels, and the graduated reduction in power may be implemented by reducing power to increasing numbers of subsets.

Some embodiments of the present invention may apply a similar delay, or a hysteresis of comparator 268, to that described above for the case wherein power supply 38 reverts from an out of specification state to being within specification. For example, supply 38 may initially generate a low voltage causing monitoring circuit 264 to output an out-of-range signal. After the preset time interval provided by delay module 542, PU 60 reduces the power to module 534. Supply 38 may then increase its voltage to within specification, so that circuit 264 no longer outputs the out-of-range signal. The processing unit may again access delay module 542 to retrieve a further preset time interval, which PU 60 applies before restoring power to module 534. In some embodiments the further preset time interval, applied for increasing the power to module 534, may be different from the time interval used for reducing the power to the module. Alternatively, the two time intervals may be the same.

From a review of the description above it is apparent that PU 60 and monitoring circuit 264 act as a power monitoring module which applies hysteresis to power changes introduced into circuitry 532, by incorporating the one or more time delays described above into the actions of the processing unit. The applied hysteresis eliminates any tendency of the elements of 532 to oscillate, during periods when the voltage supplied by power supply 38 fluctuates.

Figure 8:
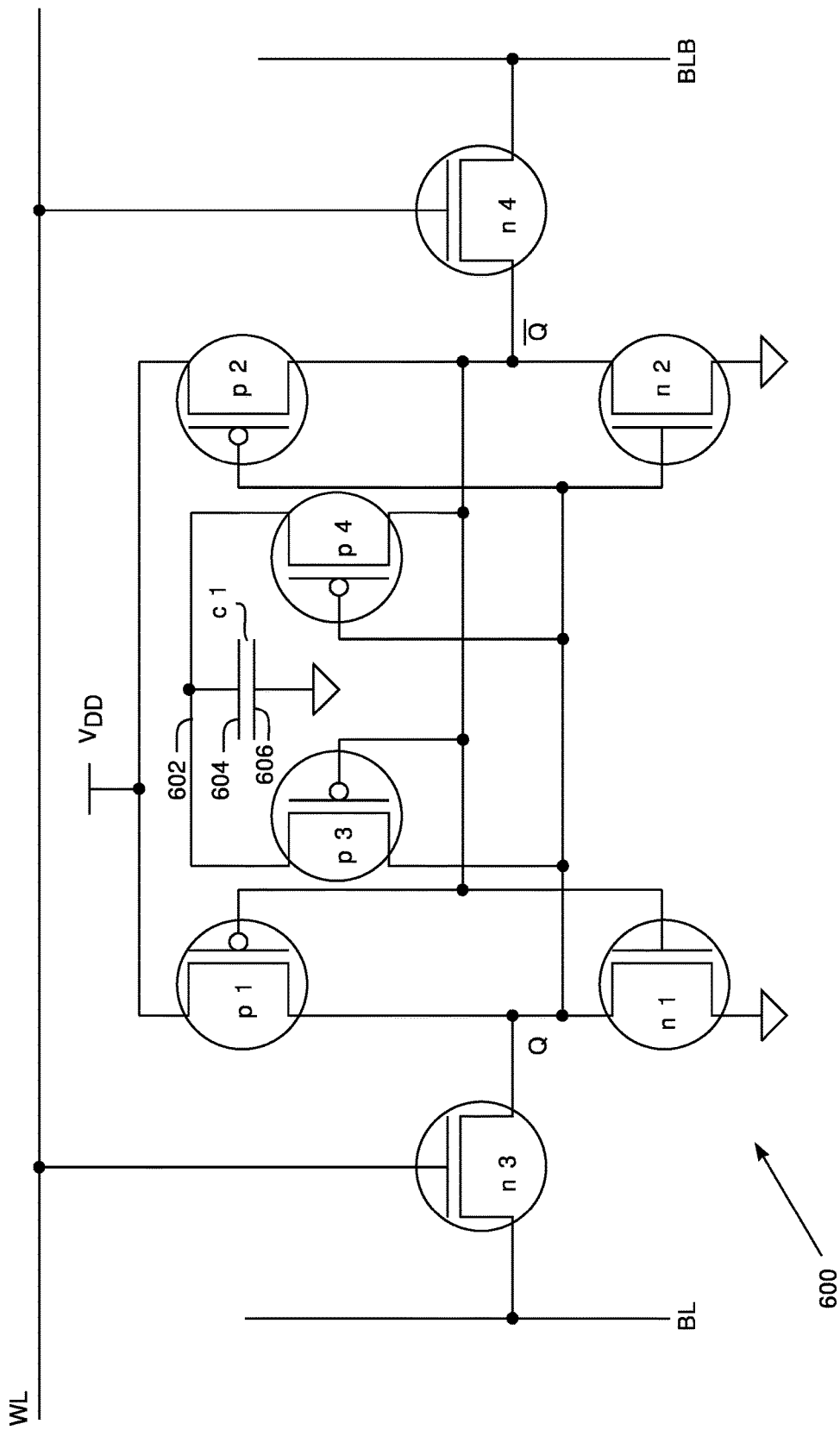
FIG. 8 is a schematic circuit diagram of a memory, according to an embodiment of the present invention.

FIG. 8 is a schematic circuit diagram of a memory 600 that may be used in any of the conversion circuitries described herein, as well as in other circuits comprising a memory, according to an embodiment of the present invention. Memory 600 is a modified version of a standard SRAM (static random access memory) cell. For clarity, in the following description of the operation of memory 600, the memory is assumed to be powered by power supply 38 (FIG. 2A), but those having ordinary skill in the art will be able to adapt the description, mutatis mutandis, for any other convenient power supply powering the memory.

Typically a plurality of memories generally similar to memory 600 are formed into a memory module, such as volatile memory 336 (FIG. 5).

Memory 600 (FIG. 8) comprises a p-type and an n-type field effect transistor (FET), p1 and n1, which are connected to form a first inverter. The gates of p1 and n1 are connected to each other and to a "$\overline{Q}$" data line. The source of n1 is connected to the drain of p1 and to a "Q" data line, the source of p1 is connected to power rail $V_{DD}$, and the drain of n1 is connected to ground rail GND.

Memory 600 also comprises a p-type FET p2 and an n-type FET n2 which are connected to form a second inverter. The gates of p2 and n2 are connected to each other and to the Q line. The source of n2 is connected to the drain of p2 and to the "$\overline{Q}$" line, the source of p2 is connected to power rail $V_{DD}$, and the drain of n2 is connected to ground rail GND.

Two n-type FETs, n3 and n4, are respectively connected to the Q and $\overline{Q}$ data lines. A WL line is connected to gates of n3 and n4, and enables the values of Q and $\overline{Q}$ to be read from and written to via respective lines BL and BLB.

A p-type FET p3 has its drain connected to the Q line, and its source connected via a floating line 602 to a first plate 604 of a capacitor c1. A second plate 606 of the capacitor is connected to ground. The gate of p3 is connected to the $\overline{Q}$ line. As explained below, capacitor c1 acts as an electrical energy storage device, supplying the voltage required to memory 600 for a limited period of time (e.g., during an eye blink, saccade, or short period up to 30, 200, or 1000 ms, c1 typically having a value of about 100-1000 femtofarads).

However, capacitor c1 is only one possible example of a suitable electrical energy storage device for the memory, and other suitable storage devices that are capable of supplying voltage and that may substitute for capacitor c1 will be apparent to those having ordinary skill in the art. Such other devices include, but are not limited to, chemical batteries or photovoltaic cells, and all such devices are assumed to be comprised within the scope of the present invention.

A p-type FET p4 has its drain connected to the $\overline{Q}$ line, and its source connected via line 602 to first plate 604. The gate of p4 is connected to the Q line.

While power supply 38 supplies its specified voltage VDD to memory 600, FETs p1, n1, p2, n2, n3, and n4 act as a single bit memory, the values of lines Q and $\overline{Q}$ taking the values of 1 or 0, depending on the values input on lines BL and BLB. In addition, one of FETs p3 or p4 conducts while the other FET does not conduct. The conduction maintains plate 604 in a charged state.

If power supply 38 changes so that the voltage $V_{DD}$ supplied is low, typically below the threshold voltage of transistors p1 and p2 (and even if $V_{DD}$ is zero), then capacitor c1 begins to discharge through the FET, p3 or p4, conducting at the time when the power supply is below the voltage in floating line 602. The out of specification situation typically occurs when $V_{DD}$ is a few tens or hundreds of millivolts. The out of specification situation may occur when $V_{DD}$ is below $V_{MIN}$ (FIG. 1B and FIG. 2B), for example below the value of $V_{MIN}$ of the first, second or third disclosed embodiments described above in reference to FIG. 1B. The discharge maintains the potential of the line Q or $\overline{Q}$ which is receiving the charge from plate 604, until the capacitor has completely discharged.

Without the presence of capacitor c1 and FETs p3 and p4, data loss may be caused once $V_{DD}$ drops below a predetermined voltage, which is proportional to an offset voltage created by any mismatch between the first and second invertors. While the mismatch may be theoretically limited, in practice processing variations may generate an offset. Applying the combination of capacitor c1 with FETs p3 and p4 allows data to be maintained in memory 600 even when voltage $V_{DD}$ is extremely low or even zero, for a limited period of time (e.g., tens or hundreds of milliseconds).

The length of time for which the data may be maintained is dependent on the capacitance of c1, and on the resistance offered by FETs p3 and p4. Thus for a high capacitance and resistance the time over which the data may be maintained is of the order of tens or more milliseconds after a complete power down of VDD. Capacitor c1 may be implemented by any convenient method, such as by separating two polysilicon layers by a silicon dioxide dielectric (a poly-poly capacitor) or by separating two metal layers by a dielectric. Alternatively or additionally, capacitor c1 may be at least partially implemented using the gate of a transistor, by methods well known in the art.

The description above has assumed that capacitor c1 supplies charge to a single memory, memory 600. In alternative embodiments of the present invention a single capacitor is configured to supply charge to a plurality of memories, substantially similar to memory 600, each having eight transistors as illustrated in FIG. 8. In the alternative embodiments, line 602 is connected as a shared floating power supply line to the sources of the respective FETs p3, p4 in each of the plurality of memories.

Figure 9:
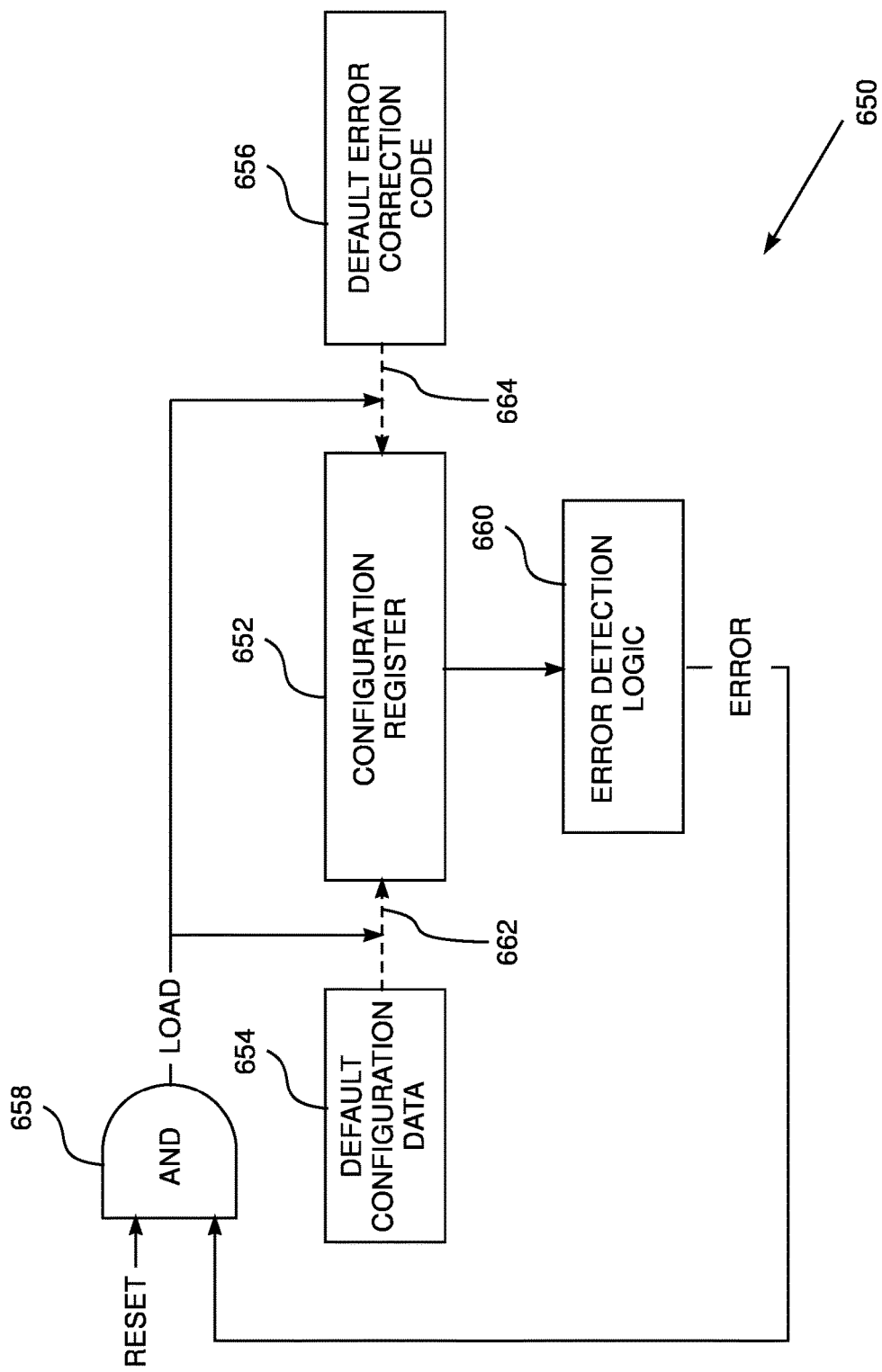
FIG. 9 is a schematic block diagram of data loading circuitry, according to an embodiment of the present invention.

FIG. 9 is a schematic block diagram of data loading circuitry 650 that may be used in any of the conversion circuitries described herein, according to an embodiment of the present invention. Typically, during powering up of a circuit, data is loaded into volatile memory comprised in the circuit. Once the data has been loaded into the volatile memory, the circuit is able to function correctly. Usually, while the circuit is functioning, the data in the volatile memory is updated as circuit conditions change.

Data loading circuitry 650 applies a condition to the data loading that may be implemented during powering up of a circuit. For clarity and by way of example, in the following description of circuitry 650, the data loading circuitry is assumed to be comprised in conversion circuitry 332 (FIG. 5). The data loading circuitry comprises a volatile configuration register 652 (which is typically part of volatile memory 336) as well as default configuration code data 654 and default error correction code data 656 which are typically stored in a non-volatile manner in operating circuitry 62. Configuration code data 654 defines a configuration of the circuit being powered up.

Circuitry 650 is implemented so that when power supply 38 powers up, a RESET signal is applied to a first input of an AND gate 658. The RESET signal may be derived by monitoring a clock activity, such as by an adaptation of monitoring circuit 264 (FIG. 4A), or by monitoring a voltage level such as by an adaptation of monitoring circuit 164 (FIG. 3). Such adaptations, mutatis mutandis, will be apparent to those having ordinary skill in the art. Alternatively, the RESET signal may be derived from any other convenient monitoring system known in the art.

In addition to applying the RESET signal, once power supply 38 has powered up an error detection logic module 660 checks the data values stored in register 652. Module 660 typically comprises parity checking or error detection logic, which may be implemented by CMOS logic circuits. If module 660 detects an error in the data values it outputs an ERROR signal to a second input of AND gate 658.

If AND gate 658 receives both the RESET and the ERROR signals, it outputs a LOAD signal. However, no LOAD signal is output if only one of, or if neither of, the RESET and the ERROR signals are received by the AND gate. The LOAD signal is used, typically by PU 60 in conversion circuitry 332, to load default configuration data 654 and default error correction code data 656 into register 652.

It will be understood that data loading circuitry 650 only allows necessary loading of data into register 652, as illustrated by broken arrows 662 and 664, and that loading only occurs if there is an error detected in the checked data. The data loading circuitry prevents unnecessary loading of data into the register, reduces demands on power supply 38, and typically only permits new configuration data to be loaded into the configuration register if the voltage supplying the circuit being powered up is equal to or above a preset limit.

Furthermore, the circuitry prevents the configuration register from accepting and using wrong or incorrect configuration data. Such incorrect data could be loaded, absent circuitry 650, if the voltage powering the circuit is low enough, for example below the value of $V_{MIN}$ of the first, second or third disclosed embodiments described above in reference to FIG. 1B. In these cases, the wrong configuration data would adversely affect the configuration of the circuit being powered up. The unnecessary loading prevented by the data loading circuitry has no negative effects on the circuitry, such as conversion circuitry 332, in which it is implemented.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus comprising:
a power supply; and
power monitoring circuitry, configured to monitor the power supply, and comprising:
a clock configured to generate a clock signal using power supplied by the power supply;
a capacitor configured to receive a current, so as to charge the capacitor;
a switching device, connected to the capacitor, configured to discharge the capacitor at fixed time intervals in response to receipt of the clock signal; and
a comparator, configured (a) to perform the monitoring of the power supply by performing a comparison of a voltage developed by the capacitor with a threshold voltage, and (b) to output an indication of a reduction in power supplied by the power supply when the switching device ceases to discharge the capacitor at the fixed time intervals due to the reduction in power.

2. The circuitry according to claim 1, wherein the current comprises a fixed charging current, and wherein the circuitry comprises a constant current generator supplying the fixed charging current.

3. The circuitry according to claim 1, wherein the threshold voltage is determined in response to a level attained by the capacitor if the capacitor is not discharged.

4. The circuitry according to claim 1, wherein the comparator is configured to output the indication if a voltage of the power supply is less than a lower threshold.

5. The circuitry according to claim 4, wherein the comparator is configured to output the indication if the voltage of the power supply is less than the lower threshold, the lower threshold being less than 1.5 volts.

6. The circuitry according to claim 5, wherein the comparator is configured to output the indication if the voltage of the power supply is less than the lower threshold, the lower threshold being between 0.2 volts and 0.6 volts.

7. A method for monitoring a power supply, the method comprising:
configuring a capacitor to receive a current, so as to charge the capacitor;
discharging the capacitor at fixed time intervals in response to receipt of a clock signal from a clock that uses power supplied by the power supply; and
performing a comparison of a voltage developed by the capacitor with a threshold voltage, and outputting an indication of a reduction in power supplied by the power supply in response to a ceasing of the discharging of the capacitor at the fixed time intervals due to the reduction in power.

8. The method according to claim 7, wherein the current comprises a fixed charging current supplied by a constant current generator.

9. The method according to claim 7, wherein the threshold voltage is determined in response to a level attained by the capacitor if the capacitor is not discharged.

10. The method according to claim 7, wherein outputting the indication comprises outputting the indication if a voltage of the power supply is less than a lower threshold.

11. The method according to claim 10, wherein outputting the indication comprises outputting the indication if the voltage of the power supply is less than the lower threshold, the lower threshold being less than 1.5 volts.

12. The method according to claim 11, wherein outputting the indication comprises outputting the indication if the voltage of the power supply is less than the lower threshold, the lower threshold being between 0.2 volts and 0.6 volts.

* * * * *